United States Patent

Ludwig et al.

[11] Patent Number: 5,990,143
[45] Date of Patent: Nov. 23, 1999

[54] WATER-BASED, SOLVENT- AND EMULSIFIER-FREE MICROBICIDAL ACTIVE COMPOUND COMBINATION

[75] Inventors: Georg-Wilhelm Ludwig, Krefeld; Otto Exner, Ratingen; Karl-Heinz Büchel, Burscheid; Graham Holmwood, Wuppertal, all of Germany

[73] Assignee: Bayer Aktiengesellschaft, Leverkusen, Germany

[21] Appl. No.: 08/416,945

[22] Filed: Apr. 4, 1995

Related U.S. Application Data

[63] Continuation of application No. 08/202,715, Feb. 23, 1994, abandoned, which is a continuation of application No. 07/942,554, Sep. 9, 1992, abandoned.

[30] Foreign Application Priority Data

Sep. 19, 1991 [DE] Germany .............................. 41 31 205

[51] Int. Cl.$^6$ .......................... A01N 25/22; A01N 33/12; A01N 43/653; A01N 47/10
[52] U.S. Cl. .......................... 514/383; 514/478; 514/479; 514/643; 514/970
[58] Field of Search ..................... 514/383, 643, 514/478, 479, 970

[56] References Cited

U.S. PATENT DOCUMENTS

| | | | |
|---|---|---|---|
| 3,934,025 | 1/1976 | Swered et al. ........................... | 514/643 |
| 4,379,709 | 4/1983 | Margold .................................... | 8/94.18 |
| 4,532,341 | 7/1985 | Holmwood et al. ..................... | 549/559 |
| 4,626,595 | 12/1986 | Holmwood et al. ..................... | 549/559 |
| 4,723,984 | 2/1988 | Holmwood et al. ........................ | 71/76 |
| 4,789,746 | 12/1988 | Kraatz et al. ............................ | 548/262 |
| 4,871,390 | 10/1989 | Holmwood et al. ........................ | 71/92 |
| 4,888,049 | 12/1989 | Iwasaki et al. ........................... | 514/567 |
| 4,897,107 | 1/1990 | Holmwood et al. ........................ | 71/92 |
| 4,904,298 | 2/1990 | Holmwood et al. ........................ | 71/92 |
| 4,911,746 | 3/1990 | Holmwood et al. ........................ | 71/92 |
| 5,196,407 | 3/1993 | Goletz et al. .............................. | 514/63 |
| 5,200,421 | 4/1993 | Ludwig et al. .......................... | 514/383 |

FOREIGN PATENT DOCUMENTS

| | | |
|---|---|---|
| 0052424 | 5/1982 | European Pat. Off. . |
| 0237764 | 9/1987 | European Pat. Off. . |
| 0393746 | 4/1990 | European Pat. Off. . |

OTHER PUBLICATIONS

McCutcheon's, Detergents and Emulsifiers 1971 Annual pp. 22 and 41.
Chemical Abstracts, Jul. 23, 1990, p. 98. 113:2 S, 798 t.
Chemical Patents Index, Basic Abstracts Journal, 1986, 86–239113/37.
Chemical Patents Index, Documentation Abstracts Journal, Mar. 13, 1991, 91–007802/02.

*Primary Examiner*—John Pak
*Attorney, Agent, or Firm*—Sprung Kramer Schaefer & Briscoe

[57] ABSTRACT

New microbicidal, optionally solvent- and emulsifier-free microbicidal active compound combinations and agents comprising known azole fungicides and quaternary ammonium compounds and their use in the preservation of materials.

5 Claims, No Drawings

WATER-BASED, SOLVENT- AND EMULSIFIER-FREE MICROBICIDAL ACTIVE COMPOUND COMBINATION

This application is a continuation of application Ser. No. 08/202,715, filed on Feb. 23, 1994 now abandoned which is a continuation application Ser. No. 07/942,554 filed on Sep. 9, 1992 now abandoned.

The present invention relates to new, in particular aqueous and optionally organic solvent- and emulsifier-free microbicidal active compound combinations comprising known azole fungicides and quaternary ammonium fungicides.

It is known that imidazole fungicides or triazole fungicides, such as, for example, α-[2-(4-chlorophenyl)-ethyl]-α-(1,1-dimethylethyl)-1-H-1,2,4-triazole-1-ethanol (tebuconazole), 2-(1-chlorocyclopropyl)-1-(2-chlorophenyl)-3-(1,2,3-triazol-1-yl)-propan-2-ol and 1-[[2-(2,4-dichlorophenyl)-4-n-propyl-1,3-dioxolan-2-yl]-methyl]-1-H-1,2,4-triazole (propiconazole), can be used as such or in the form of their salts for protecting plants and seeds (compare, for example, EP-A 0,040,345 and EP-A 0,052,424).

It is furthermore known that these compounds are also suitable for use in the preservation of materials for combating microbes which destroy materials or discolour materials (compare, for example, DE-OS (German Published Specification) U.S. Pat. No. 3,621,494 and U.S. Pat. No. 4,079,062).

However, the azole fungicides, such as the tebuconazole mentioned, have gaps in their action on some germs relevant to the preservation of materials, such as, for example, Trichoderma spec.

Because of the often low water-solubility of azoles, their use in some fields of application, such as, for example, leather, water-based wood preservatives, disinfection, cooling water treatment, paper industry, metal processing and industrial preservation of water-containing products, is furthermore limited or impossible.

Quaternary ammonium salts have been known for a long time as microbicides having a broad action and are used, for example, in disinfection and preservation of textiles.

Although these active compounds are usually readily water-soluble, they tend to foam severely at the use concentrations, which causes trouble in many fields of use. Furthermore, because of their cationic properties, they can react with anionic components, such as soaps, surfactants and the like. This can adversely influence their profile of properties, or they may become deactivated. It is furthermore known that quaternary ammonium salts can easily be deactivated by the presence of protein and dirt.

For many uses in the practice of preservation of materials, it is desirable to employ the active compounds in liquid formulations which are free from organic solvents or in which the corresponding solvent content is drastically reduced.

Water-insoluble solvents are incompatible with aqueous products such as leather liquors, emulsion paints, cooling and process water and disinfectants.

The users are often also not equipped to handle products in the form of solutions in organic solvents, since particular devices, associated with high investment costs, are necessary for application from the solvent and for recovery thereof, which is essential to avoid ecological problems.

Water-soluble solvents would in principle be suitable as solubilising agents in aqueous systems. However, if they enter the waste water, they can cause ecological problems.

Furthermore, solvents can manifest themselves adversely in the products to be preserved.

Another possibility of solubilisation for the preparation of water-based active compound formulations is to use emulsifiers. In the case of highly water-insoluble compounds, such as azoles, large amounts of emulsifier are as a rule needed for this, which is to be avoided for ecological reasons. The activity of the microbicidal active compound can likewise be severely impaired by the use of emulsifiers. The usefulness for certain systems may also be limited.

The object of the invention was therefore to provide new, preferably water-based, solvent- and emulsifier-free microbicidal active compound formulations based on azole fungicides, which can be diluted easily with water and then give storage-stable solutions for use.

It has now been found, surprisingly, that stable aqueous solutions or emulsions which have a particularly high microbicidal activity can be prepared by combination of at least one azole fungicide in the form of the free base, preferably 1-(4-chlorophenoxy)-3,3-dimethyl-1-(1H-1,2,4-triazo-1-yl)-2-butanones (triadimefon)

β-(4-chlorophenoxy)-α-(1,1-dimethyl-ethyl)-1H-1,2,4-triazole-1-ethanol (triadimenol)

±α-[2-(4-chlorophenyl)-ethyl]-α-(1,1-dimethylethyl)-1H-1,2,4-triazole-1-ethanol (tebuconazole)

(RS)-2-(2,4-dichlorophenyl)-1-(1H-1,2,4-triazol-1-yl)-hexan-2-ol (hexaconazole)

1-(N-propyl-N-(2-(2,4,6-(trichlorophenoxy)-ethyl)-carbamoyl)-imidazole (prochloraz), 2-(1-chlorocyclopropyl)-1-(2-chlorophenyl)-3-(1,2,4-triazol-1-yl)-propan-2-ol 1-[[2-(2,4-dichlorophenyl)-4-propyl-1,3-dioxolon-2-yl]-methyl]-1H-1,2,4-triazole (propionazole)

1-[2-(2,4-dichlorophenyl)-1,3-dioxolon-2-yl-methyl]-1H-1,2,4-triazole (azaconazole)

the isomers and isomer mixtures of the most diverse compositions also being included in the cases where the compounds have asymmetric carbon atoms;

especially preferably ±α-[2-(4-chlorophenyl)-ethyl]-α-(1,1-dimethylethyl)-1H-1,2,4-triazole-1-ethanol (tebuconazole) and at least one quaternary ammonium fungicide, preferably of the formula (II)

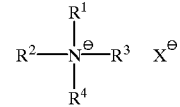

in which

R$^1$, R$^2$, R$^3$ and R$^4$ are identical or different and in each case represent unsubstituted or substituted, straight-chain or branched, saturated or unsaturated alkyl groups having 1–20 carbon atoms, alkylaryl and aralkyl groups having 5–10 carbon atoms in the aryl part and 1–20 carbon atoms in the alkyl part or aryl groups having 5–10 carbon atoms, and optionally mono-or polyalkoxylated derivatives hereof; possible substituents being halogen, C$_1$–C$_4$-alkyl and C$_1$–C$_4$-alkoxy; and wherein 2 or 3 radicals R$^1$ to R$^4$ on the quaternary centre, optionally with further hetero atoms, can form a saturated or unsaturated 5-, 6- or 7-membered (hetercyclic) ring and X represents an anion which promotes water-solubility, such as, for example, halide, sulphate, alkylsulphonate or optionally substituted arylsulphonate.

Such aqueous formulations avoid the abovementioned ecological and use-related disadvantages of solvent-based or emulsifier-mediated formulations and in this respect are a useful enrichment of the prior art.

Quaternary ammonium compounds which may be mentioned as preferred are ammonium salts such as
$C_{12}$–$C_{14}$-alkyl-benzyl-dimethylammonium chloride
trimethyl-coconut-ammonium chloride
didecyldimethylammonium chloride.

$C_{12}$–$C_{14}$-Alkyl-benzyl-dimethylammonium chloride is particularly preferred.

As already mentioned, the azole fungicides are in the form of their free base.

A combination of tebuconazoles and $C_{12}$–$C_{14}$-alkyl-benzyldimethylammonium chloride is especially preferred.

The weight ratios of the active compounds in the active compound combinations can be varied within relatively wide ranges.

They depend in general on the field of use and on the particular azole and guaternary ammonium fungicides employed. However, these weight ratios can easily be determined in test series by simply mixing the components.

The weight ratio of azole fungicide to quaternary ammonium fungicide is preferably 1:99 to 99:1, in particular 1:40 to 9:1, particularly preferably 1:20 to 1:1 and especially preferably 1:10 to 1:2. To prepare aqueous formulations, the active compounds are incorporated individually or as an active compound combination, for example in the form of powders, granules, pastes or concentrated solutions, suspensions or emulsions, into water by simple mixing, and are then present in the form of an aqueous suspension, solution or emulsion.

The aqueous solutions or emulsions preferably contain more than 20% by weight, in particular more than 40% by weight of water and can be diluted with water as desired to the use concentration. It is of course also possible for the active compounds or active compound combination in the form of concentrates, solutions, suspensions, emulsions, powders, granules or pastes to be incorporated directly in the amounts required for use, for example by stirring into the agent to be used.

The microbicidal agents contain the active compound combination in a concentration of 0.001 to 95% by weight, in particular 0.01 to 60% by weight, and in addition optionally 0.001 to 30% by weight, in particular 0.01 to 20% by weight, especially 0.05–10% by weight, of a suitable additional fungicide, insecticide or an additional active compound.

The active compound combinations or agents according to the invention have a potent action against microorganisms. They are used in the preservation of materials for preserving industrial materials; they are active above all against moulds, wood-discolouring and wood-destroying fungi and bacteria and against yeasts, algae and slime organisms. The following genera of microorganisms may be mentioned as examples—but without making a limitation:

Alternaria, such as *Alternaria tenuis*, Aspergillus, such as *Aspergillus niger* and *Aspergillus terreus*, Aureobasidium, such as *Aureobasidium pullulans*, Chaetomium, such as *Chaetomium globosum*, Cladosporium, such as *Cladosporium herbarum*, Coniophora, such as *Coniophora puteana*, Gliocladium, such as *Gliocladium virens*, Lentinus, such as *Lentinus tigrinus*, Paecilomyces, such as *Paecilomyces varioti*, Penicillium, such as *Penicillium brevicaule, Penicillium glaucum* and *Penicillium pinophilum*, Polyporus, such as *Polyporus versicolor*, Sclerophoma, such as *Sclerophoma pityophila*, Streptoverticillium, such as *Streptoverticillium reticulum*, Trichoderma, such as *Trichoderma viride* and Trichophyton, such as *Trichophyton mentagrophytes*;

Escherichia, such as *Escherichia coli*, Pseudomonas, such as *Pseudomonas areuginosa*, and Staphylococcus, such as *Staphylococcus aureus*; and Candida, such as *Candida albicans*.

The amount of active compound combinations employed depends on the nature and the occurrence of the microorgnanisms of the germ count and on the medium. The optimum amount to be employed during use can be determined in each case by test series. In general, however, it is sufficient to employ 0.001 to 20% by weight, preferably 0.05 to 10% by weight of the active compound mixtures, based on the material to be preserved.

The new active compound combinations can be used as such or in the form of concentrates or generally customary formulations, such as powders, granules, solutions, suspensions, emulsions or pastes.

The formulations mentioned can be prepared in a manner which is known per se, for example by mixing the active compounds with a solvents or diluents, emulsifiers, dispersing agents and/or of binder or fixing agent, if appropriate siccatives and UV stabilisers and if appropriate dyestuffs and pigments as well as other processing auxiliaries.

Possible solvents or diluents are organochemical solvents or solvent mixtures and/or a polar organic solvent or solvent mixtures and/or an oily or oil-like organochemical solvent or solvent mixture and/or water with at least one emulsifier and/or wetting agent. Customary water-insoluble oily or oil-like solvents of low volatility which are used are, preferably, the particular mineral oils/solvent mixtures containing mineral oils or aromatic fractions thereof. Examples which may be mentioned are white spirit, petroleum or alkylbenzenes, and in addition spindle oil and monochloronaphthalene. The boiling ranges of these (mixtures of) solvents of low volatility spread over the range from about 170° C. to not more than 350° C.

The oily or oil-like solvents of low volatility described above can be partly replaced by organochemical solvents of higher volatility.

To prepare a wood preservative, some of the solvent or solvent mixture described above is replaced by a polar organochemical solvent or solvent mixture. Solvents which contain hydroxyl groups, ester groups, ether groups or mixtures of this functionality are preferably employed here. Esters or glycol ethers may be mentioned as examples. Binders are understood according to the invention as binding drying oils or synthetic resins which are water-dilutable or soluble, dispersible or emulsifiable in organochemical solvents, and for example those based on acrylic resins, vinyl resins, polyester resins, polyurethane resins, alkyl resins, phenolic resins, hydrocarbon resins or silicone resins. The binder used can be employed as a solution, emulsion or dispersion. Mixtures of alkyd resins and a drying vegetable oil are preferably used. Alkyd resins having an oil content of between 45 and 70% are particularly preferred.

All or some of the binder mentioned can be replaced by a fixing agent (mixture) or a plasticiser (mixture). These additives are intended to prevent evaporation of the active compounds and crystallisation or precipitation. They preferably replace 0.01 to 30% of the binder (based on 100% of the binder employed).

The plasticisers originate from the chemical classes or phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stereate and amyl stereate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether, or ketones, such as benzophenone and ethylbenzophenone.

A possible solvent or diluent is preferably water, if appropriate mixed with one or more of the abovementioned solvents or diluents, emulsifiers and dispersing agents.

According to the invention, industrial materials are non-living materials which have been prepared for use in industry. Industrial materials which are to be preserved by active compounds according to the invention against microbial change or destruction can be, for example, adhesives, sizes, paper and card, textiles, leather, wood, paints and articles made of plastic, cooling lubricants and other materials which may be attacked or decomposed by microorganisms. Components of production plants, for example cooling water circulations, which may be impaired by multiplication of microorganisms may also be mentioned in the context of the materials to be preserved. Preferred industrial materials in the context of the invention are adhesives, sizes, papers and cards, leather wood, paints, cooling lubricants, aqueous hydraulic fluids and cooling circulations.

The active compound combinations, agents or concentrates according to the invention are preferably employed for preserving wood and timber products against microorganisms, for example against wood-destroying or wood-discolouring fungi, in particular in tropical wood preservation.

By wood which can be preserved by the mixtures according to the invention there is to be understood, for example: building timber, wooden beams, railway sleepers, bridge components, boat jetties, wooden vehicles, boxes, pallets, containers, telephone poles, wooden fences, wood panelling, wooden windows and doors, plywood, chipboard, joinery or timber products which are used quite generally in house construction or building joinery.

Particularly effective preservation of wood is achieved by large-scale impregnation processes, for example vacuum, double vacuum- or pressure processes.

The activity and the action spectrum of the active compound combinations according to the invention or the agents, concentrates or quite generally formulations which can be prepared therefrom is increased, if appropriate, if other antimicrobially active substances, fungicides, insecticides or other active compounds are added to increase the active compound spectrum or achieve particular effects, such as, for example, additional protection against insects. Particularly favourable mixing partners are, for example, the following compounds:

sulphenamides, such as dichlofluanid (Euparen), tolylfluanid (Yethyleuparen), folpet or fluorfolpet; benzimidazoles (if appropriate in the form of their salts), such as carbendazim (MBC), benomyl, fuberidazole and thiabendazole; thiocyanates, such as thiocyanatomethylthiobenzothiazole (TCYTB) and methylene bisthiocyanate (MBT); morpholine derivatives, such as $C_{11}$–$C_{14}$-4-alkyl-2,6-dimethylmorpholine homologues (tridemorph), (±)-cis-4-[3-tert.-butylphenyl)-2-methylpropyl]-2,6-dimethylmorpholine (fenpropimorph) and falimorph; phenols, such as o-phenyl-phenol, halogenated cresols, tribromophenol, tetrachlorophenol, pentachlorophenol and 3-methyl-4-chlorophenol; dichlorophen; iodopropargyl derivatives, such as iodopropargylbutylcarbamate (IPBC), -chlorophenylformal, phenylcarbamate, hexylcarbamate and cyclohexylcarbamate; isothiazolinones, such as N-methylisothiazolin-3-one, 5-chloro-N-methylisothiazolin-3-one, 4,5-dichloro-N-octylisothiazolin-3-one and N-octylisothiazolin-3-one (octhilinone); pyridines, such as 1-hydroxy-2-pyridinethione (and their Na, Fe, Mn and Zn salts) tetrachloro-4-methyl-sulphonylpyridine and tetrachloro-4-methyl-sulphonylpyridine; metal soaps, such as the naphthenate, octoate, 2-ethylhexanoate, olete, phosphate, benzoate and oxide of tin, copper or zinc; zinc salts of dialkyl-dithiocarbamates; tetramethyldiuram disulphite (TMTD); 2,4,5,6-tetrachloroisophthalonitrile (chlorothalonil); benzothiazoles, such as 2-mercaptobenzothiazole; thiazolyl-benzimidazole; quinolines, such as γ-hydroxyquinoline; benzyl alcohol mono(poly) hemiformal; and tris-N-(cyclohexyldiazeniumdioxy)-aluminium and N-(cyclohexyldiazeniumdioxy)-tributyltin.

Insecticides which are preferably added are:

phosphoric acid esters, such as azinphos-ethyl, azinphosmethyl, 1-(4-chlorophenyl)-4-(O-ethyl,S-propyl)phosphoryloxy-pyrazole (TIA-230), chlorpyrifos, coumaphos, demeton, demeton-S-methyl, Diazinon, dichlorvos, dimethoate, ethoprophos, etrimfos, fenitrothion, fention, heptenophos, parathion, parathion-methyl, phosalone, phoxion, pirimiphos ethyl, pirimiphos methyl, profenofos, prothiofos, sulprofos, triazophos and trichlorophone;

carbamates, such as aldicarb, bendiocarb, BPMC (2-(1-methylpropyl)phenyl methylcarbamate), butocarboxim, butoxycarboxim, carbaryl, carbofuran, carbosulphan, cloethocarb, isoprocarb, methomyl, oxamyl, pirimicarb, promecarb, propoxur and thiodicarb;

pyrethroids, such as allethrin, alphamethrin, bioresmethrin, byfenthrin (FMC 54 800), cycloprothrin, cyfluthrin, decamethrion, cyhalothrin, cypermethrin, deltamethrin, alpha-cyano-3-phenyl-2-methylbenzyl 2,2-dimethyl-3-(2-chloro-2-trifluoromethylvinyl)cyclopropanecarboxylate, fenpropathrin, fenfluthrin, fenvalerate, flucythrinate, flumethrin, fluvalinate, permethrin and resmethrin; and nitroimides, such as 1-[(6-chloro-3-pyridinyl)-methyl]-4,5-dihydro-N-nitro-1H-imidazol-2-anine (imidacloprid).

Possible other active compounds are algicides, molluscicides and active compounds against "sea animals" which colonise on, for example, ship's bottom paints.

The active compound combinations and agents according to the invention advantageously allow the microbicidal agents hitherto available to be replaced by more effective and more environmentally compatible agents. They display a good stability and advantageously have a broad action spectrum.

The following examples serve to illustrate the invention without limiting it thereto. Parts and percentage data denote parts by weight and percentages by weight.

EXAMPLES 42.5 g of $C_{12}$–$C_{14}$-alkyl-benzyldimethylammonium chloride are initially dissolved in 42.5 g of water. This solution is heated to 60° C. and 15 g of tebuconazole are added. The mixture is stirred at this temperature until a clear solution is formed.

Example 2

5.5 g of a powder mixture consisting of 4.5 g of $C_{12}$–C14-alkyl-benzyldimethylammonium chloride and 1.0 g of tebuconazole are stirred into 94.5 g of water. A clear solution is obtained by stirring at about 60° C.

Example 3

42.5 g of $C_{12}$–$C_{14}$-alkyl-benzyldimethylammonium chloride are initially dissolved in 42.5 g of water. This solution is heated to 60° C. and 10 g of tebuconazole are added. 5.0 g of iodopropargyl butylcarbamate are also stirred into this clear solution and dissolved to form a clear solution.

Example 4

30.0 g of $C_{12}$–$C_{14}$-alkyl-benzyldimethylammonium chloride are dissolved and initially introduced into 30.0 g of water. 30.0 g of ethyl acetate are added to this solution and the mixture is homogenised by stirring. 10.0 g of tebuconazole are stirred into the solution, which has been heated to about 60° C., and are dissolved to form a clear solution.

We claim:

1. A ready-to-use formulation comprising a fungicidally effective amount of a stable solution comprising:
   a) ±α-[2-(4-chlorophenyl)-ethyl]-α-(1,1-dimethylethyl)-1H- 1,2,4-triazole-1-ethanol (tebuconazole);
   b) iodopropargyl butylcarbamate;
   c) water; and
   d) $C_{12}$–$C_{14}$-alkyl-benzyl-dimethylammonium chloride.

2. A method of combating fungi which comprises applying to said fungi or to a habitat from which it is desired to exclude said fungi a fungicidally effective amount of a formulation according to claim 1.

3. A method of protecting wood from fungi which comprises applying to said wood a protective amount of a formulation according to claim 1.

4. A method of protecting leather from fungi which comprises applying to said leather a protective amount of a formulation according to claim 1.

5. A concentrate intended to be diluted with water to form a ready-to-use fungicidical formulation, said concentrate comprising a fungicidally effective amount of a stable solution comprising:
   a) ±α-[2-(4-chlorophenyl)-ethyl]-α-(1,1-dimethylethyl)-1H-1,2,4-triazole-1-ethanol (tebuconazole);
   b) iodopropargyl butylcarbamate;
   c) water; and
   d) $C_{12}$–$C_{14}$-alkyl-benzyl-dimethylammonium chloride.

* * * * *